United States Patent
Durgin (10) Patent No.: US 7,077,821 B2
(45) Date of Patent: Jul. 18, 2006

(54) IMPLANT SYSTEM AND METHOD FOR BULKING TISSUE

(75) Inventor: Russell Durgin, Attleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/442,932

(22) Filed: May 22, 2003

(65) Prior Publication Data

US 2003/0192558 A1    Oct. 16, 2003

Related U.S. Application Data

(62) Division of application No. 09/110,125, filed on Jul. 6, 1998, now Pat. No. 6,591,838.

(51) Int. Cl.
*A61M 31/00* (2006.01)
(52) U.S. Cl. .............................. 604/60; 604/57; 604/59
(58) Field of Classification Search ............ 604/11–18, 604/104, 358, 369, 374; 606/151, 167, 200, 606/213, 191–199
See application file for complete search history.

(56) References Cited

U.S. PATENT DOCUMENTS

| | | | |
|---|---|---|---|
| 1,969,671 A | 8/1934 | Nelson | |
| 3,138,159 A | 6/1964 | Schmidt | |
| 3,805,786 A | 4/1974 | Bernardin et al. | |
| 3,965,905 A | 6/1976 | Schoenholz et al. | |
| 4,183,102 A | 1/1980 | Guiset | |
| 4,439,872 A | 4/1984 | Henley-Cohn et al. | |
| 4,636,213 A | 1/1987 | Pakiam | |
| 4,740,208 A | 4/1988 | Cavon | |
| 4,769,011 A | 9/1988 | Swaniger | |
| 4,775,646 A | 10/1988 | Hench et al. | |
| 4,790,819 A | 12/1988 | Li et al. | |
| 4,820,303 A | 4/1989 | Brauman | |
| 4,895,559 A | 1/1990 | Shippert | |
| 4,900,304 A | 2/1990 | Fujioka et al. | |
| 4,955,907 A | 9/1990 | Ledergerber | |

(Continued)

FOREIGN PATENT DOCUMENTS

EP    0 628 292 A1    12/1994

(Continued)

OTHER PUBLICATIONS

Fleischer, David E., et al., "Tissue band ligation followed by snare resection (band and snare): a new technique for tissue acquisition in the esophagus", Gastrointestinal Endoscopy, vol. 44, No. 1, 1996, pp. 68-72.

(Continued)

*Primary Examiner*—Glenn K. Dawson
(74) *Attorney, Agent, or Firm*—Finnegan Henderson Farabow Garrett & Dunner, L.L.P.

(57) ABSTRACT

A system for placing an implant in the body includes an elongated member having at least one inner lumen extending from a proximal end portion of the member to an opening in a distal end portion of the member. At least one compressible implant is in the inner lumen of the member. The implant optionally includes anchor members projecting from its outer surface to limit migration of the implant in the body. Structure is provided to push the implant through the opening in the distal end portion of the member. The implant is placed between layers of body tissue to bulk the tissue. In one of the disclosed methods, the system is used to treat gastroesophageal reflux disease (GERD) by placing the implant between layers of body tissue at or near the gastroesophageal junction.

9 Claims, 10 Drawing Sheets

U.S. PATENT DOCUMENTS

| | | | |
|---|---|---|---|
| 4,955,909 A | 9/1990 | Ersek et al. | |
| 4,963,150 A | 10/1990 | Brauman | |
| 4,994,028 A | 2/1991 | Leonard et al. | |
| 5,002,583 A | 3/1991 | Pitaru et al. | |
| 5,021,059 A * | 6/1991 | Kensey et al. | 606/213 |
| 5,067,965 A | 11/1991 | Ersek et al. | |
| 5,116,357 A * | 5/1992 | Eberbach | 606/213 |
| 5,176,692 A * | 1/1993 | Wilk et al. | 606/151 |
| 5,192,302 A * | 3/1993 | Kensey et al. | 606/213 |
| 5,201,704 A | 4/1993 | Ray | |
| 5,290,310 A * | 3/1994 | Makower et al. | 606/213 |
| 5,304,123 A | 4/1994 | Atala et al. | |
| 5,310,407 A | 5/1994 | Casale | |
| 5,336,163 A | 8/1994 | DeMane et al. | |
| 5,336,263 A * | 8/1994 | Ersek et al. | 424/422 |
| 5,391,183 A * | 2/1995 | Janzen et al. | 606/213 |
| 5,395,308 A * | 3/1995 | Fox et al. | 604/15 |
| 5,399,351 A | 3/1995 | Leshchiner et al. | |
| 5,403,326 A | 4/1995 | Harrison et al. | |
| 5,437,631 A * | 8/1995 | Janzen | 604/506 |
| 5,447,499 A | 9/1995 | Allaire et al. | |
| 5,531,759 A * | 7/1996 | Kensey et al. | 606/213 |
| 5,545,141 A * | 8/1996 | Eld | 604/170.03 |
| 5,554,185 A | 9/1996 | Block et al. | |
| 5,571,116 A | 11/1996 | Bolanos et al. | |
| 5,658,330 A | 8/1997 | Carlisle et al. | |
| 5,667,778 A | 9/1997 | Atala | |
| 5,728,178 A * | 3/1998 | Buffington et al. | 604/115 |
| 5,766,181 A | 6/1998 | Chambers et al. | |
| 5,779,734 A | 7/1998 | Ledergerber | |
| 5,827,215 A | 10/1998 | Yoon | |
| 5,993,445 A * | 11/1999 | Issa | 606/46 |
| 6,098,629 A | 8/2000 | Johnson et al. | |
| 6,174,315 B1 | 1/2001 | Chambers et al. | |
| 6,214,045 B1 * | 4/2001 | Corbitt et al. | 623/8 |
| 6,523,542 B1 * | 2/2003 | Knudson et al. | 128/897 |
| 6,547,724 B1 * | 4/2003 | Soble et al. | 600/156 |
| 6,591,838 B1 * | 7/2003 | Durgin | 128/898 |

FOREIGN PATENT DOCUMENTS

| | | |
|---|---|---|
| SU | 1 655 469 A1 | 6/1991 |
| WO | WO 95/00184 | 1/1995 |

OTHER PUBLICATIONS

Tada, M., et al., "Endoscopic Resection of Early Gastric Cancer", Endoscopy 1993; 25: pp. 445-450.

O'Connor, Katherine W., MD, et al., "An experimental endoscopic technique for reversing gastroesophageal reflux in dogs by injecting inert material in the distal esophagus", Gastrointestinal Endoscopy, vol. 30, No. 5, 1984, pp. 275-280.

O'Connor Katherine W., MD, et al., "Endoscopic placement of collagen at the lower esophageal sphincter to inhibit gastroesophageal reflux: a pilot study of 10 medically intractable patients", Gastrointestinal Endoscopy, vol. 34, No. 2, 1988, pp. 106-112.

* cited by examiner

IMPLANT SYSTEM AND METHOD FOR BULKING TISSUE

Divisional Application under 37 C.F.R. § 1.53(b) of prior Application No. 09/110,125 filed Jul. 6, 1998 now U.S. Pat. No. 6,591,838 of Russell DURGIN for IMPLANT SYSTEM AND METHOD FOR BULKING TISSUE

BACKGROUND OF THE INVENTION

1. Field of the Invention

The present invention relates to an implant and a system and method for placing the implant in the body to bulk body tissue. More particularly, the present invention relates to a system and method for placing the implant at or near the gastro-esophageal junction to treat gastroesophageal reflux disease (GERD).

2. Description of Related Art

The lower esophageal sphincter is located in a distal portion of the esophagus adjacent to the junction between the esophagus and the stomach. When food is digested, a properly functioning lower esophageal sphincter allows food to pass from the esophagus to the stomach while limiting reverse flow of the stomach contents into the esophagus.

Gastroesophageal reflux disease (GERD) is a disorder in which the lower esophageal sphincter allows contents of the stomach including gastric acid and bile to reverse flow into the distal portion of the esophagus. Complications associated with GERD include heartburn, pulmonary disorders, chest pain, esophageal ulcers, esophagitis, Barrett's esophagus, and esophageal carcinoma.

A common treatment for GERD includes administering prescription acid blockers for limiting gastric production of acid. Although these drugs may provide short term relief, the drugs merely alleviate some of the symptoms of GERD rather than correcting the underlying dysfunction of the lower esophageal sphincter. In addition, acid blockers are expensive, and any long term complications associated with using acid blockers are unknown.

Various surgical procedures have been attempted to correct GERD. In one surgical procedure, known as Nissen fundoplication, a portion of the gastric fundus is wrapped around the esophagus. The wrapped gastric fundus applies pressure to the esophagus to limit reverse flow of the stomach contents into the esophagus. Conventional fundoplication procedures are effective at treating GERD, but they have a number of disadvantages. Open procedures require a large incision to expose the stomach and the lower esophagus. In laparoscopic procedures, four or five smaller incisions are formed in the abdominal wall to insert instruments into the body of the patient. However, such procedures are expensive and sometimes require a significant amount of time for patient recovery.

Some other procedures, such as those disclosed in U.S. Pat. No. 5,403,326 and in U.S. Pat. No. 5,571,116, use surgical staples to secure the fundus of the stomach and the lower esophagus. However, some of the relatively rigid stapling instruments used in these procedures may damage tissue when they are moved in a patient. In addition, such rigid instruments are inserted into the operative field with trocar type devices which make abdominal wall penetrations. These abdominal wall penetrations increase the risks of post-operative hernias, accidental organ perforations, or other drawbacks associated with laparoscopic surgery.

Bulking the tissue of the digestive track at or below the gastro-esophageal junction is a relatively recent, investigative treatment for GERD. In one such treatment, collagen in a saline carrier is placed in the tissue around the gastro-esophageal junction to cause partial closure of the distal end of the esophagus and thereby prevent gastric acid from reaching the esophageal mucosa. Although the collagen could provide short term benefits, it eventually becomes absorbed by the body and loses it effectiveness.

Bulking of body tissue is also performed in a number of other treatments and procedures. For example, tissue is bulked in cosmetic surgical procedures and in treatments for urinary incontinence. However, the current implants and devices for inserting them have a number of disadvantages when they are used for tissue bulking.

In light of the foregoing, there is a need in the art for an improved implant, implantation system, and tissue bulking procedure.

SUMMARY OF THE INVENTION

Accordingly, the present invention is directed to an implant, system and method that substantially obviate one or more of the limitations of the related art. To achieve these and other advantages and in accordance with the purpose of the invention, as embodied and broadly described herein, the invention includes a system for placing an implant in the body. The system comprises an elongated member and at least one compressible implant in an inner lumen of the member. The implant is configured to be implanted in body tissue to bulk the tissue. Structure is provided for pushing the implant through an opening in a distal end portion of the member.

In an aspect of the invention, the structure for pushing the implant includes a pushing member movable in the inner lumen or a source of fluid for pressurizing the inner lumen.

In another aspect, the elongated member has a first lumen for the implant and a second lumen for passing fluid into the body to separate tissue layers.

In still another aspect, the implant includes structure for limiting migration of the implant in the body.

In a further aspect, the present invention includes a method of bulking tissue. In this method, the elongated member is introduced in the body. The distal end portion of the elongated member is positioned between layers of body tissue. A pushing force is applied to the implant to move the implant through the opening in the distal end portion and between the layers of body tissue.

In yet another aspect, the method includes placing fluid between the layers of body tissue to separate the layers of body tissue.

In an even further aspect, a plurality of compressible implants are in the inner lumen of the elongated member, and more than one of the compressible implants are placed between the layers of tissue.

In one other aspect, the implant is placed between body tissue layers at or near the gastro-esophageal junction to treat GERD.

In an additional aspect, the present invention includes an implant formed of compressible material. Anchor members project from the outer surface of the implant. The anchor members are configured to interconnect with anchor members on another implant implanted in the body.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Reference will now be made in detail to the present preferred embodiments of the invention, examples of which are illustrated in the accompanying drawings. Wherever possible, the same reference numbers are used in the drawings and the description to refer to the same or like parts, and similar reference numerals are used to refer to similar elements.

Figure 1:
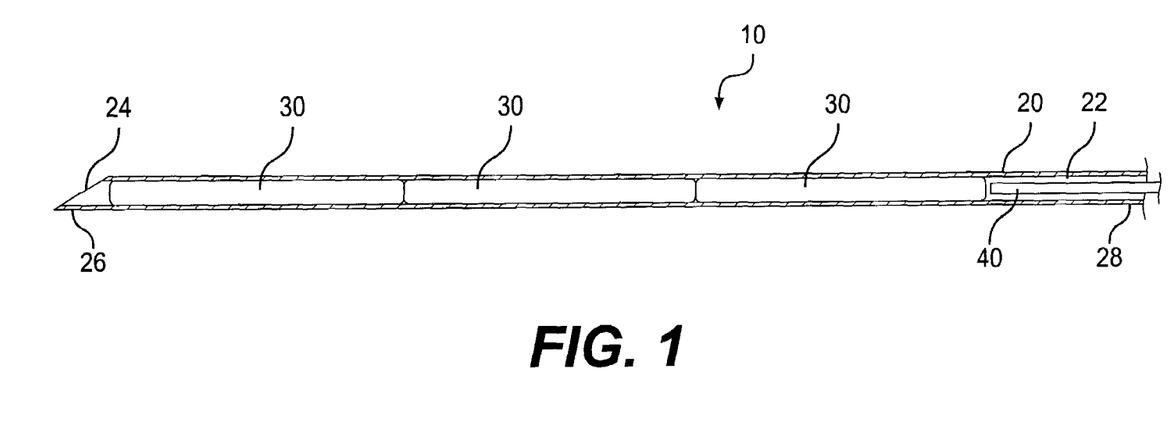
FIG. 1 is partial cross sectional view of an implant placement system according to a first embodiment of the invention.
Figure 2:
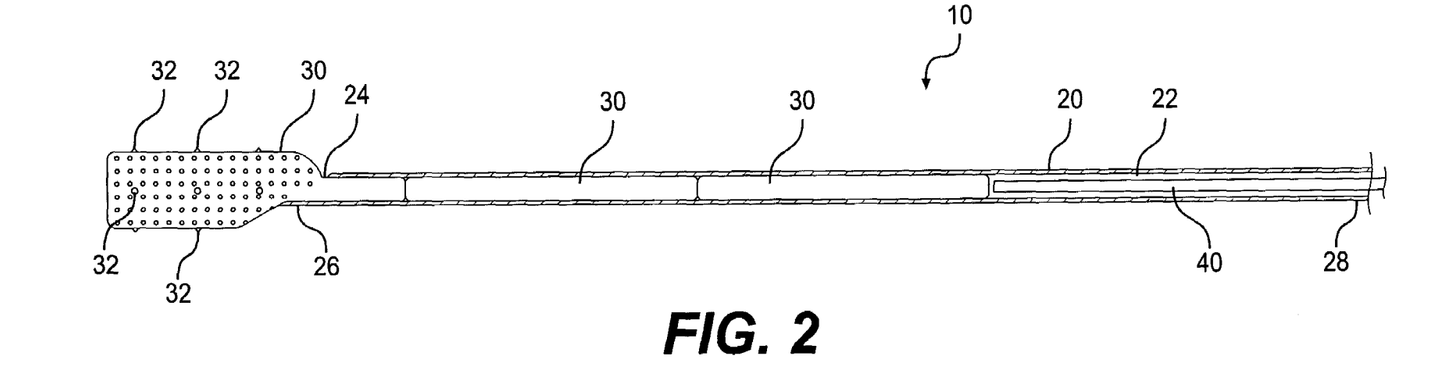
FIG. 2 is a view similar to that of FIG. 1 with an implant of the system partially pushed through a distal end opening of an elongated member shown in FIG. 1.

FIGS. 1 and 2 show an implant placement system 10 according to a first embodiment of the invention. As shown in FIGS. 1 and 2, the system 10 includes an elongated member 20 having an inner lumen 22, one or more implants 30 in the inner lumen 22, and a pushing member 40 for pushing the implants 30 through both the lumen 22 and an opening 24 in a distal end portion of the elongated member 20.

Figure 11:
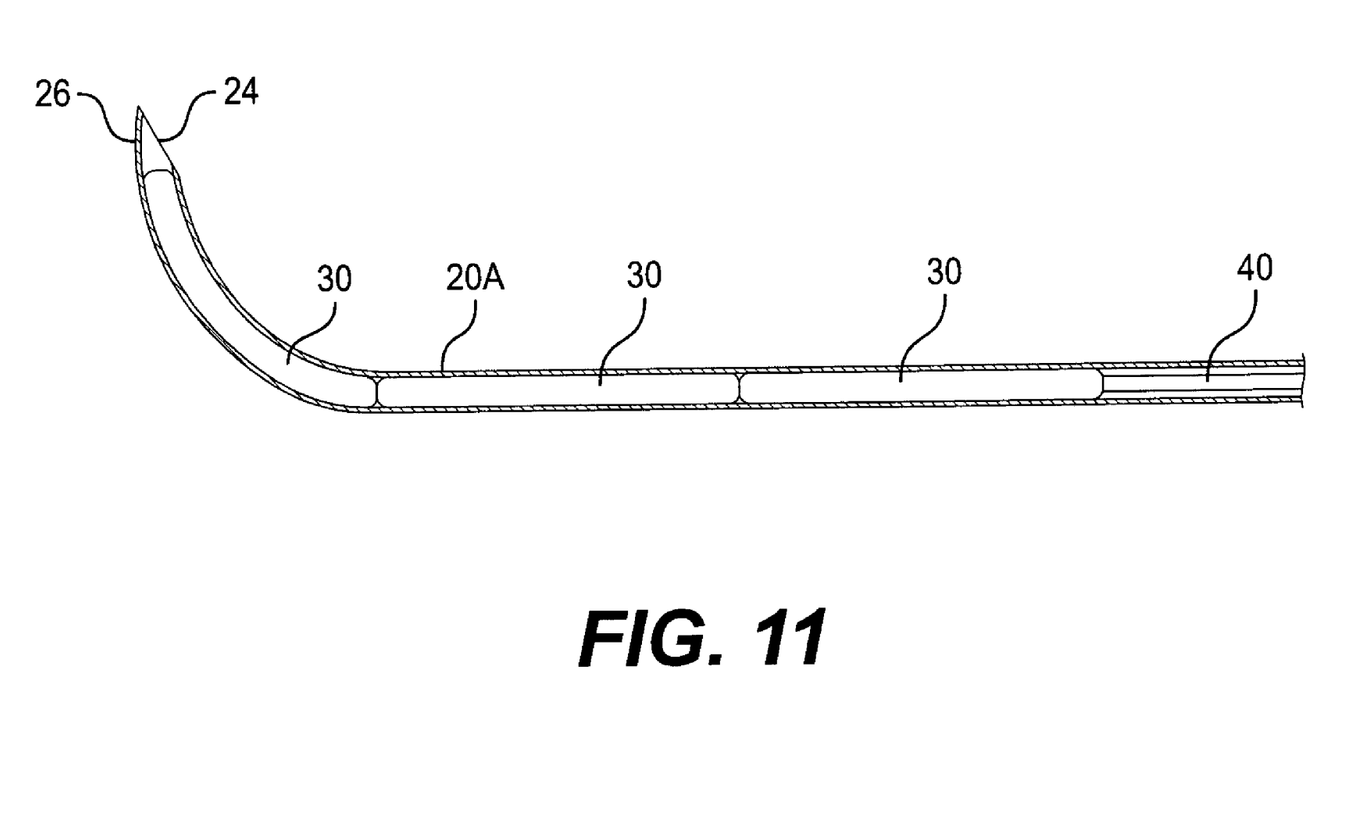
FIG. 11 is a view similar to FIG. 1 showing an embodiment of a curved implant insertion member.

The elongated member 20 is preferably a hollow needle, cannula, or tubular member having a sharpened distal end 26 configured to pierce though layers of body tissue so that the opening 24 can be positioned between the tissue layers. When the opening 24 is located in this position, one or more of the implants 30 are ejected from the opening 24 and become implanted between the tissue layers. As described below, the elongated member 20 is preferably long enough to be passed transorally through the esophagus during a GERD treatment procedure to position the distal end portion of the elongated member 20 between layers of tissue at or near the gastro-esophageal junction. To allow for such passage through the esophagus without significant trauma, the elongated member 20 preferably has a sufficient amount of flexibility, and is optionally precurved or bent in a shape facilitating placement of the distal end 26 at a desired location in the body. For example, FIG. 11 shows an embodiment of an elongated member 20A having a curved distal end portion.

The elongated member 20 could be formed of many different types of material, but materials, such as radiopaque materials, which are capable of being detected with conventional medical imaging equipment, are preferred. In a preferred embodiment, the elongated member 20 includes bands or stripes of material capable of being visualized to determine how far the elongated member 20 is inserted in the body.

The inner lumen 22 preferably extends from a proximal end 28 of the elongated member 20 to the opening 24 in the distal end 26. The cross section of the inner lumen 22 could have many different shapes, however a generally circular cross sectional shape is preferred. Preferably, the surface of the inner lumen 22 is relatively smooth to allow for sliding of the implants 30 therethrough.

The pushing member 40 has an outer cross sectional size smaller than the cross sectional size of the inner lumen 22 to allow the pushing member 40 to move axially in the inner lumen 22. Preferably, the pushing member 40 is a cylindrical-shaped push rod having a length slightly longer than that of the elongated member 20. When at least one of the implants 30 and the pushing member 40 are in the inner lumen 22, distal movement of the pushing member 40 with respect to the elongated member 40 forces the implants 30 through the inner lumen 22 and through the distal end opening 24. To facilitate manipulating the pushing member 40 and the elongated member 20, the proximal ends of both the pushing member 40 and the elongated member 20 preferably include a respective handle (not shown).

Figure 3:
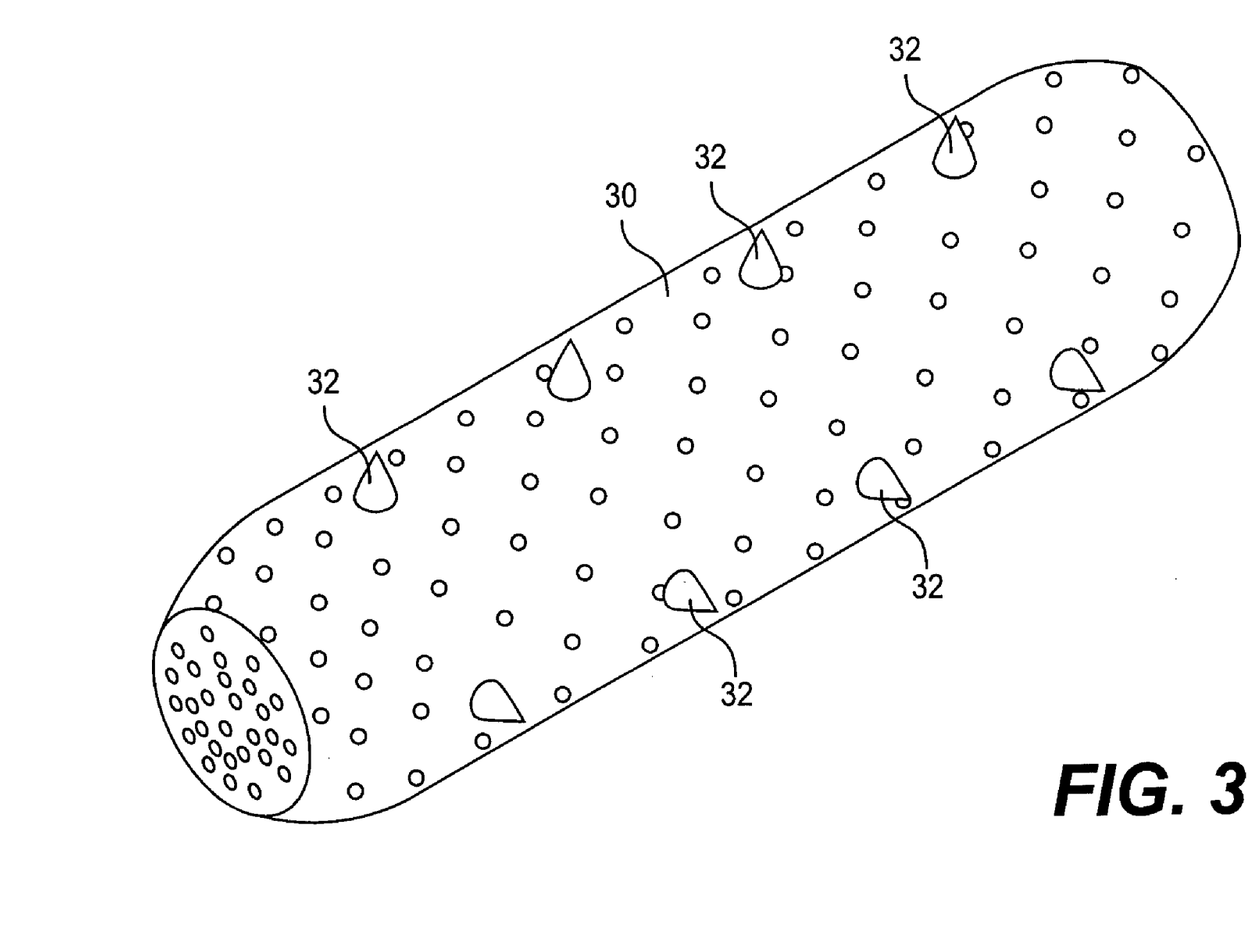
FIG. 3 is a perspective view of one of the implants shown in FIGS. 1 and 2.

FIG. 3 shows the preferred configuration of the implant 30. The implant 30 is preferably made of a flexible, compressible material, capable of being compressed into a reduced size permitting the implant 30 to be stored in the inner lumen 22, and also permitting the implant 30 to expand resiliently back to its original size after the implant 30 passes through the distal end opening 24, as shown in FIG. 2.

Because the implant 30 is capable of being compressed into a reduced size while it is in the inner lumen 22, the outer cross sectional size of the elongated member 20 is reduced as compared to insertion devices for non-compressible implants. Preferred materials for forming the implant include urethane, silicone, and fluoropolymer.

Preferably, the implant 30 is formed of open cell foam and/ or closed cell foam having a number of internal void areas. The use of closed cell foam isolates antibody attack to the outer surface of the foam to preserve the foam's flexibility and compressibility. Closed cell foam also reduces significant tissue ingrowth to maintain the flexibility of the implant 30. Open cell foam, on the other hand, permits tissue and collagen growth in pores of the foam to reduce migration of the implant 30 in the body.

In an alternative embodiment, the implant 30 is formed of an elastomeric material and has a hollow cavity filled with a fluid, such as air. Forming the implant 30 with such a material and cavity permits the implant 30 to be placed in the inner lumen 22 and to maintain its shape after being implanted. in the body without the need to be inflated.

To permit imaging of the implant 30, the implant 30 preferably includes radiopaque material capable of being detected with conventional imaging equipment.

As shown in FIG. 3, the implant 30 preferably has a generally cylindrical shape with rounded ends. In another preferred embodiment (not shown), the implant 30 has a substantially spherical shape. The implant 30 could also be shaped in many other ways. For example, the implant 30 could be have a polygonal shaped cross section, such as a triangular shaped cross section. When the implant 30 is cylindrical and in its expanded form, the implant 30 preferably has a length of from about 100 thousandths of an inch to about 250 thousandths of an inch, and a diameter of from about 50 thousandths of an inch to about 175 thousandths of an inch, for example.

Preferably, the outer surface of the implant 30 includes structure for limiting migration of the implant 30 when the implant 30 is implanted in the body. In the embodiment of the implant 30 shown in FIG. 3, the implant 30 includes anchor members 32 extending from the outer surface of the implant 30. The anchor members 32 preferably have a pointed or rounded end capable of engaging body tissue.

Figure 12:
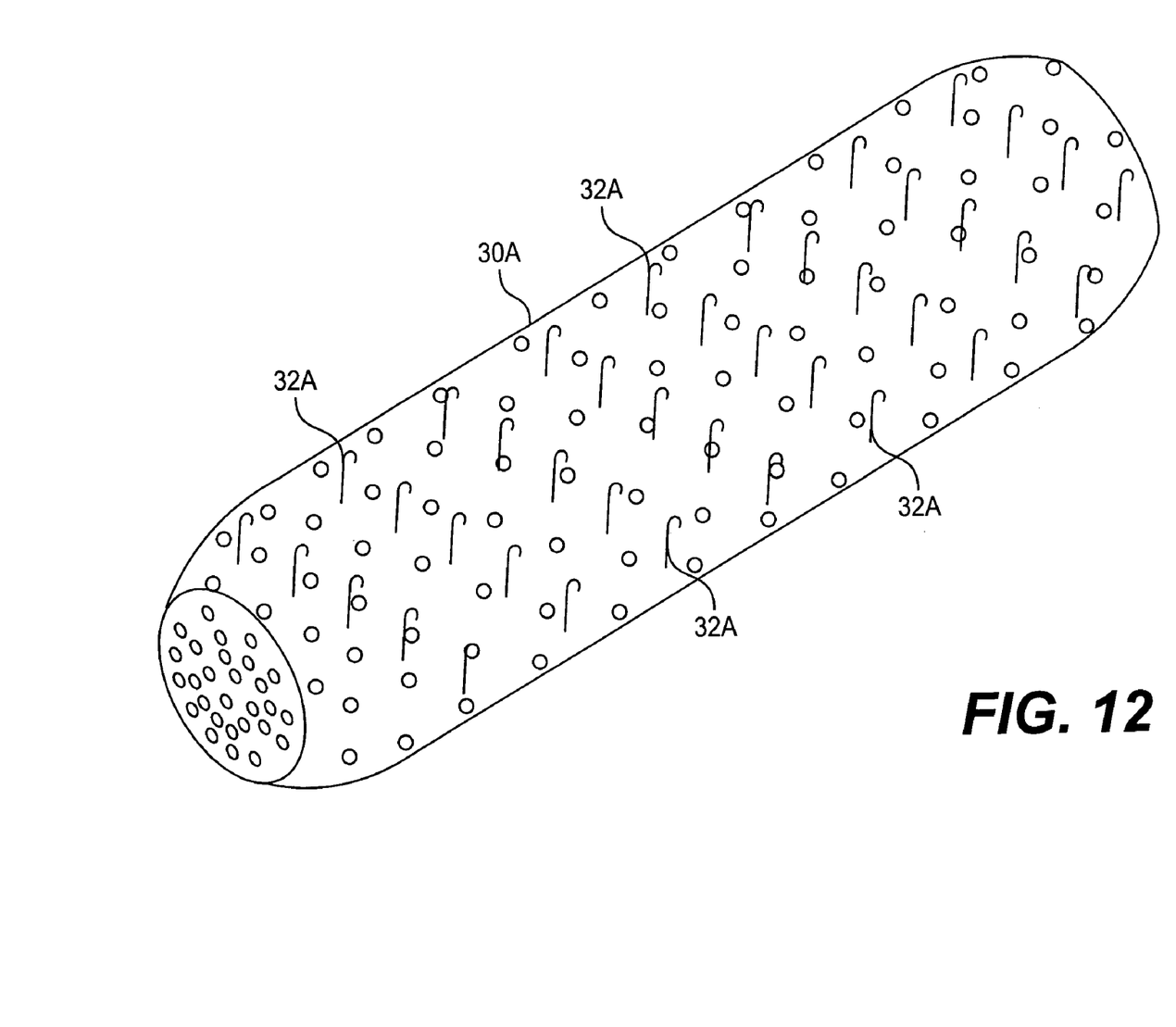
FIG. 12 is a view similar to FIG. 3 showing an embodiment of the implant having hook-shaped anchors.

FIG. 12 shows an alternative embodiment of an implant 30A. The implant 30A includes anchor members 32A in the form of hook-shaped projections. In addition to being configured to engage tissue, the anchor members 32A are also configured to interconnect with corresponding hook-shaped projection anchors 32A on one or more other implants 30A to form coupled groups of the implants 30A. Optionally, the anchor members 32 and 32A are formed of a bioabsorbable material capable of being absorbed in the body after tissue growth around the implant 30, 30A is sufficient.

Figure 13:
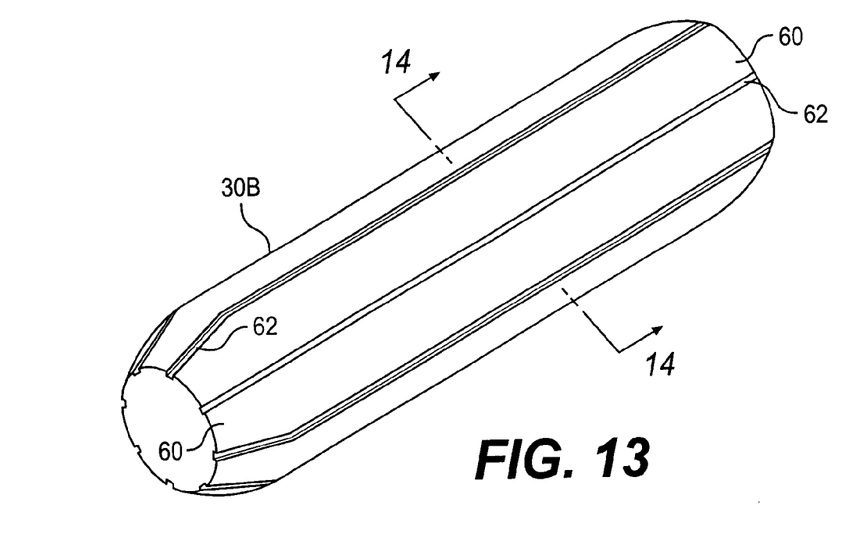
FIG. 13 is a view similar to FIG. 3 showing an embodiment of the implant having longitudinal ridges and grooves.
Figure 14A:
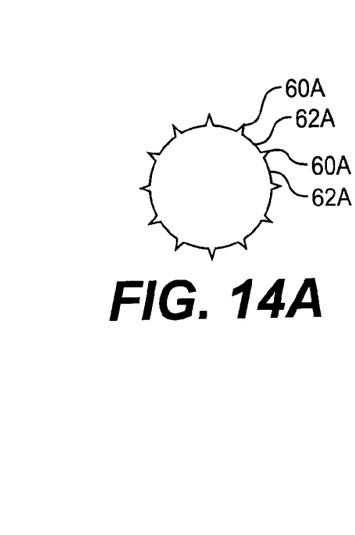
FIG. 14A is a cross-sectional view taken along line 14—14 of FIG. 13 showing a first alternative ridge and groove shape for the implant of FIG. 13.
Figure 14B:
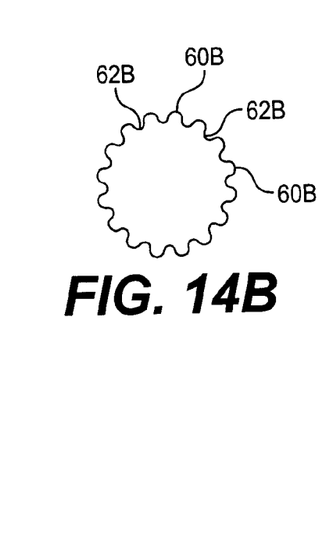
FIG. 14B is a view similar to FIG. 14A showing a second alternative ridge and groove shape.
Figure 14C:
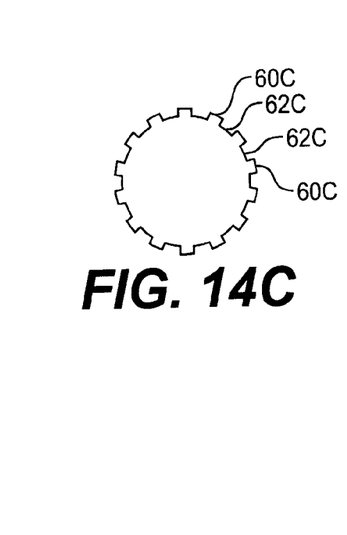
FIG. 14C is a view similar to FIG. 14A showing a third alternative ridge and groove shape.
Figure 15:
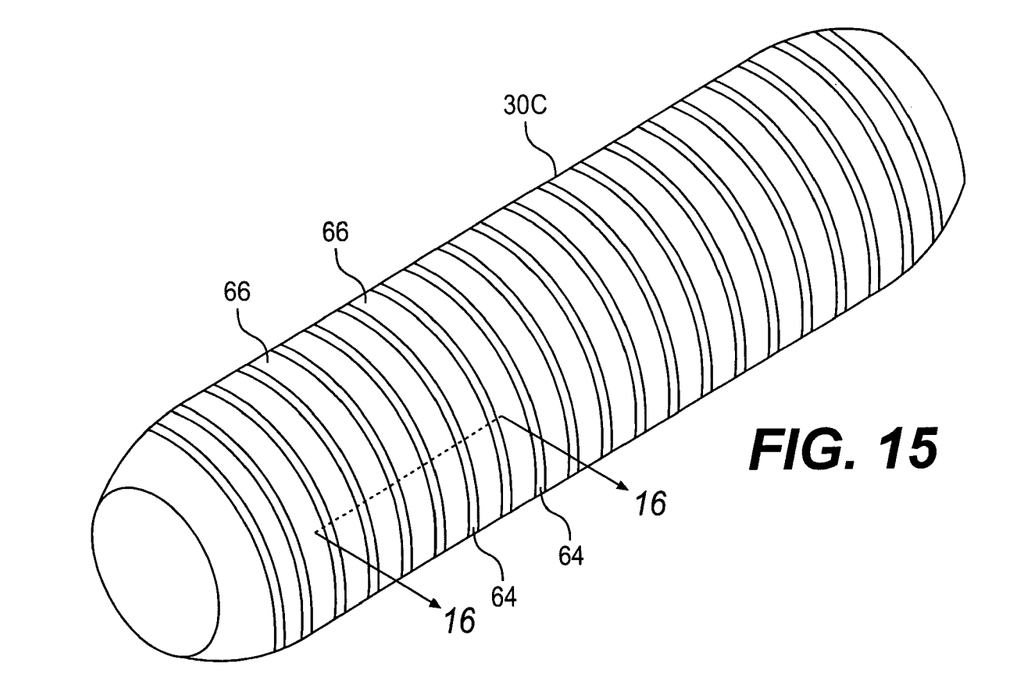
FIG. 15 is a view similar to FIG. 3 showing an embodiment of an implant having transverse ridges and grooves.
Figure 16A:
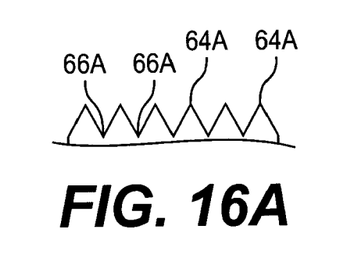
FIG. 16A is a partial cross-sectional view taken along line 16—16 of FIG. 15 showing a first alternative ridge and groove shape for the implant of FIG. 15.
Figure 16B:
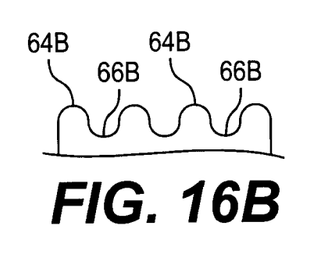
FIG. 16B is a view similar to FIG. 16A showing a second alternative ridge and groove shape.
Figure 16C:
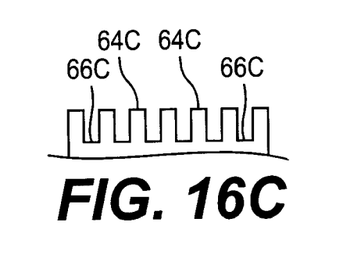
FIG. 16C is a view similar to FIG. 16A showing a third alternative ridge and groove shape.

The implant 30 could also include other structure for limiting migration. For example, the implant 30 preferably includes an outer surface coating for increasing the coefficient of friction of the implant 30. In addition, the outer surface of the implant 30 preferably includes ridges, grooves, or other surface discontinuities to reduce migration and to increase the outer surface area to induce tissue ingrowth. For example, FIG. 13 shows an embodiment of an implant 30B having longitudinal ridges 60 and grooves 62, and FIG. 15 shows an embodiment of an implant 30C having transverse ridges 64 and grooves 66. As shown in FIGS. 14A, 14B, and 14C, the implant 30B shown in FIG. 13 could have pointed ridges 60A, rounded ridges 60B, or relatively flattened ridges 60C, and either relatively flattened grooves 62A, 62C or curved grooves 62B. As shown in FIGS. 16A, 16B, and 16C, the implant 30C shown in FIG. 15 could have pointed ridges 64A, rounded ridges 64B, or relatively flattened ridges 64C, and pointed grooves 66A, rounded grooves 66B or flattened grooves 66C.

There are many different ways in which the implants 30 could be compressed into a reduced size and loaded into the elongated member 20 as shown in FIG. 1. One of the simplest ways of loading the implants in the elongated member 20 is to force the implants 30 into the inner lumen 22. In another process for loading the implants 30 in the elongated member 20, the implants 30 are reduced in size by clamping, heat shrinking, or stretching, and then the reduced size implants are cryogenically frozen. Optionally, when the implant is formed of open cell material, a soaking agent, such as water, is added to the foam material to facilitate reducing the implant's size prior to cryogenic freezing. Soon after freezing, the chilled implants are placed in the elongated member 20 so that the implants 30 are capable of expanding when they are warmed.

Other methods of initially reducing the size of the implants 20 and loading them in the elongated member 20 are possible. In one alternative method, a soaking agent is added to the implant, and the implant is heat dried while it is maintained in a reduced size. The heat drying causes the implant to remain in its reduced size until the implant comes in contact with a liquid, such as water and expands like a conventional kitchen sponge. In another alternative embodiment, the implant is placed in its reduced size by applying a vacuum to the implant.

Figure 4:
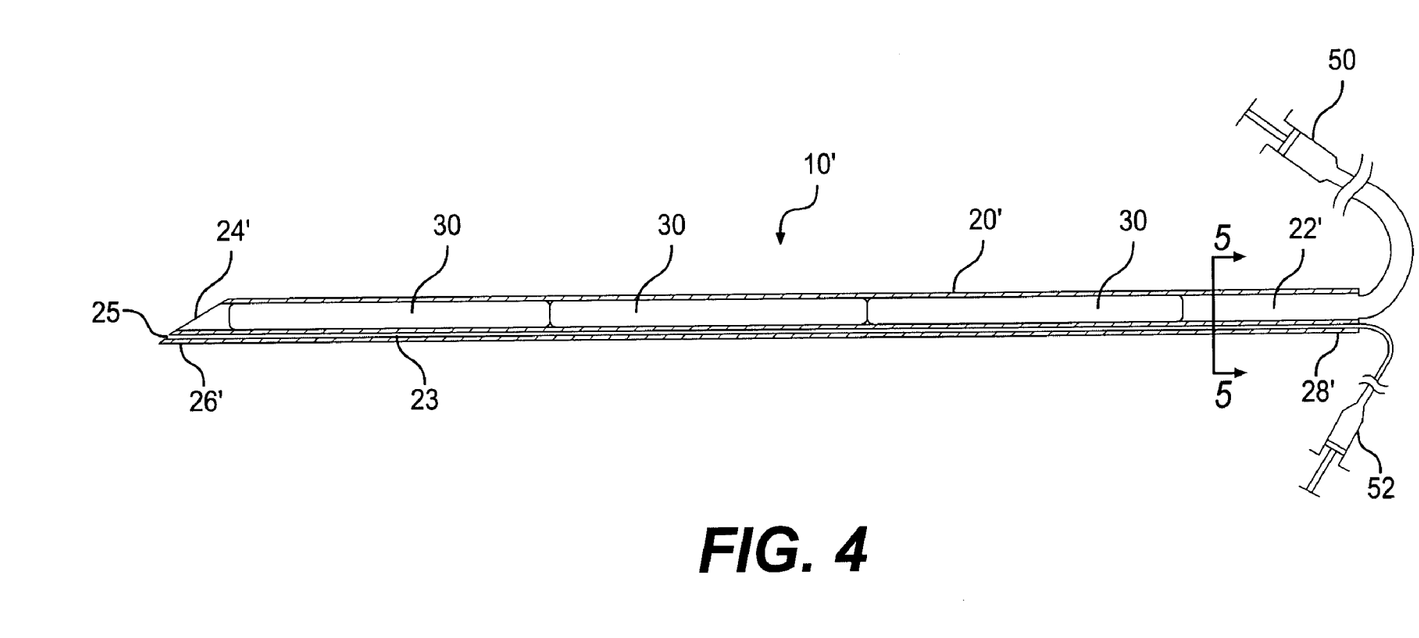
FIG. 4 is a partial cross sectional view of a second embodiment of the implant placement system.

FIG. 4 shows an alternative embodiment of a system 10' constructed similar to the system 10 shown in FIGS. 1 and 2. The system 10' shown in FIG. 4 includes an elongated member 20' having a first inner lumen 22' and a second inner lumen 23. Preferably, both the first inner lumen 22' and the second inner lumen 23 extend along the entire length of the elongated member 20'. The first inner lumen 22' preferably extends from a proximal portion 28' of the elongated member 10' to a first opening 24' in a distal end 26' of the elongated member 10'. The second inner lumen 23 preferably extends from the proximal portion 28' to a second opening 25 in the distal end 26'.

Figure 5A:
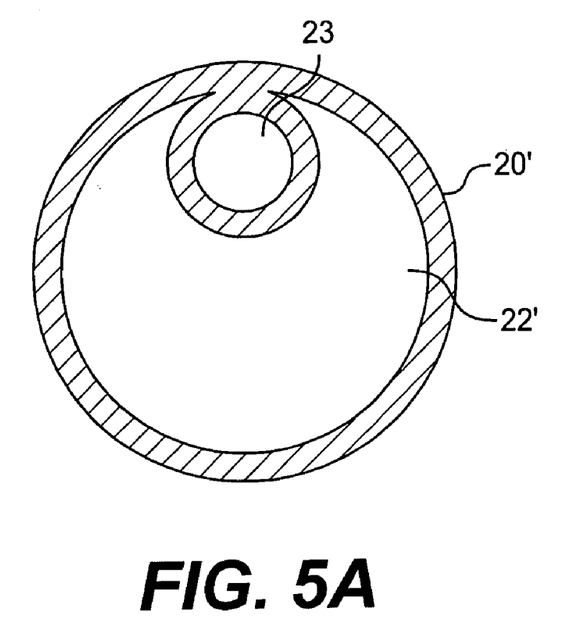
FIG. 5A is a cross sectional view taken along line 5—5 of FIG. 4.
Figure 5B:
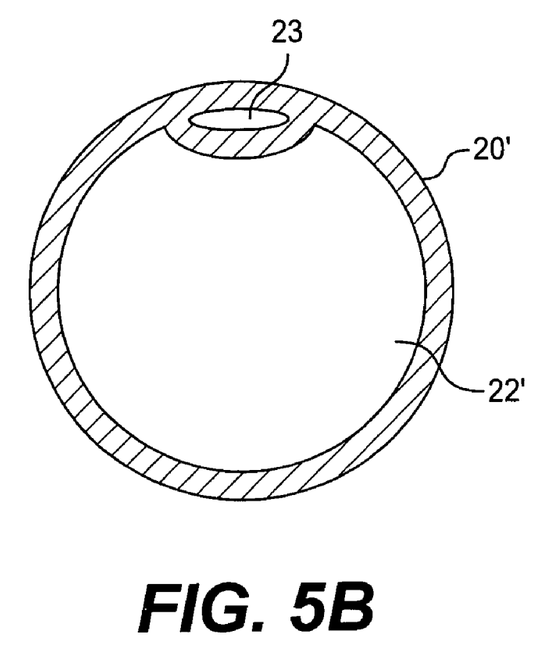
FIG. 5B is a cross sectional view similar to that of FIG. 5A showing an alternative lumen configuration for an elongated member shown in FIG. 4.

The first and second lumens 22' and 23 could have many different cross sectional shapes and sizes. As shown in FIG. 5A, the second lumen 23 could have a substantially circular cross section and be positioned partially within the first lumen 22'. Alternatively, as shown in FIG. 5B, the second lumen 23 could have a generally flattened cross sectional configuration.

Implants 30 are loaded in the first lumen 22'. To push the implants 30 through both the first inner lumen 22' and the first opening 24', the first lumen 22' is preferably pressurized with fluid. As shown in FIG. 4, a first fluid source 50 is in fluid communication with the first inner lumen 22'. The first fluid source 50 is preferably a syringe or other pumping device capable of being activated to deliver a fluid, such as saline or air, to the first inner lumen 22'. When the fluid delivered by the first source 50 increases the pressure in the first inner lumen 22', one or more of the implants 30 are forced through the first inner lumen 22' and through the first opening 24'. If the ejecting fluid is a liquid and the implant 30 is formed of open cell foam, the implant 30 preferably does not absorb an undue amount of the liquid.

In an alternative embodiment, not shown, a pushing member similar or identical to the pushing member 40 shown in FIGS. 1 and 2 is used in place of the first fluid source 50 to eject implants 30 from the opening 24'. In another alternative embodiment, not shown, the elongated member 20 shown in FIGS. 1 and 2 has its inner lumen 22 in fluid communication with a fluid source, such as the first fluid source 50, rather than having the pushing member 40.

As shown in FIG. 4, the second inner lumen 23 is preferably in flow communication with a second fluid source 52 similar or identical to the first fluid source 50. The second fluid source 52 is configured to deliver fluid, such as saline, through both the second inner lumen 23 and the second opening 25. As explained below, the fluid flowing from the second opening 25 is used to separate layers of body tissue when the distal end 26' is placed in the tissue. This separation of the layer of body tissue facilitates placement of the implants 30 between the tissue layers.

Preferably, the fluid provided by the second source 52 includes a radiopaque additive, which is capable of being detected by conventional radiographic imaging equipment. The use of the radiopaque additive permits a physician to view the location of the tissue separation provided by the fluid from the second source 52. In addition, this additive provides a visible radiographic background to allow for a physician to determine whether the distal end of the elongated member 10' is properly located.

Methods of bulking tissue to treat GERD are discussed below with reference to FIGS. 1–4 and 6–10. Although the invention is described in connection with the structure shown in these figures, and in connection with treating GERD, it should be understood that the invention in its broadest sense is not so limited.

Initially, the elongated member 10 shown in FIGS. 1 and 2 or the elongated member 10' shown in FIG. 4 is introduced into the body of a patient until the distal end 26, 26' of the elongated member 10, 10' is positioned at or near (for example, below) the gastro-esophageal junction. To reduce trauma, the elongated member 10, 10' is preferably passed transorally through the esophagus until the distal end 26, 26' is at or near the stomach. In a preferred practice of the invention, an endoscope, such as a gastrointestinal endoscope having visual imaging capability, is initially inserted transorally through the esophagus, and the elongated member 10, 10' is introduced through a working lumen of the endoscope. In order to facilitate insertion and positioning of the elongated member 10, 10', the elongated member 10, 10' is preferably positioned while a physician uses imaging equipment, such as fluoroscopic, radiographic, ultrasonic, and/or visual imaging equipment.

After the elongated member 10, 10' is inserted in the esophagus, the distal end 26, 26' of the elongated member 10, 10' is positioned between layers of body tissue at or near the gastro-esophageal junction. When the distal end 26, 26' includes a sharp tip, such as that shown in FIGS. 1, 2, and 4, the distal end 26, 26' is pierced through the layers of body tissue.

As shown schematically in FIGS. 6–10, the tissue at or near the gastro-esophageal junction J includes three primary layers—the mucosa layer A which forms the inner lining of the esophagus E and stomach S, the submucosa layer B which is the intermediate tissue layer, and the muscularis layer C which is the outermost layer. Preferably, the distal end 26, 26' shown in FIGS. 1, 2, and 4 is positioned so that the opening 24, 24' is located between the mucosa layer and the outer surface of the muscularis layer.

To facilitate proper positioning of the distal end 26, 26' between the appropriate tissue layers, fluid is preferably placed between the tissue layers to form a pocket that separates the layers of tissue. For example, when the elongated member 10' shown in FIG. 4 is used, the fluid for separating the tissue layers is delivered through the second opening 25 by the second fluid source 52. When the elongated member 10 shown in FIGS. 1 and 2 is used, a separate needle is inserted into the layers of tissue at or near the gastro-esophageal junction, and the needle is used to inject fluid, like that delivered by the second fluid source 52, between the tissue layers to separate them. Because the elongated member 10' shown in FIG. 4 includes the second inner lumen 23, a separate needle or other structure is not required to separate the tissue layers with fluid.

After optionally separating the tissue with fluid to position the distal end 26, 26', one or more of the implants 30 are ejected from the distal end opening 24, 24' by pushing the implants 30 through both the inner lumen 22, 22' and the opening 24, 24'. As the implants 30 are pushed through the opening 24, 24', they expand from their compressed configuration, as shown in FIG. 2, for example.

The way in which the implants 30 are pushed through the opening 24, 24' depends on the particular structural arrangement being used. When the elongated member 20' shown in FIG. 4 is being used, the implants 30 are pushed through the opening 24' by pressurizing the inner lumen 22' with the fluid from the first fluid source 50. When the elongated member 20 shown in FIGS. 1 and 2 is being used, the implants 30 are pushed through the opening 24 by moving the pushing member 40 distally in the inner lumen 22 and/or by retracting the elongated member 20 proximally with respect to the pushing member 40 while the pushing member 40 contacts one of the implants 30 in the inner lumen 22. Retracting the elongated member 20 is preferred in certain circumstances because the implants 30 are placed in the body at a location previous occupied by the distal end 26.

Preferably, the implants 30 are placed between the mucosa layer and the muscularis layer at or near the gastro-esophageal junction. The implants 30 could be arranged in a uniform or random manner. Preferably, the implants 30 are placed in the submucosa layer, however, the implants 30 may also be positioned in at least a portion of the muscularis layer and even the mucosa layer.

Preferably, more than one of the implants 30 is placed in the layers of tissue adjacent to or at the gastro-esophageal junction, although it could be possible to place only a single implant 30 in the tissue. The exact number of implants 30 depends on a number of factors including the expanded size of the implants 30 and the amount of tissue bulking which is required. Having a plurality of implants 30 loaded in the lumen 22, 22' limits the need to load more implants or introduce another implant insertion device.

If the implants 30 include anchor members 32, such as those shown in FIG. 3, the anchor members 32 preferably limit migration of the implants 32. When the implants include hook-shaped anchors, such as the anchors 30A shown in FIG. 12, the anchor members of adjacent implants can be interconnected to form groups of multiple implants having limited migration.

Figure 6:
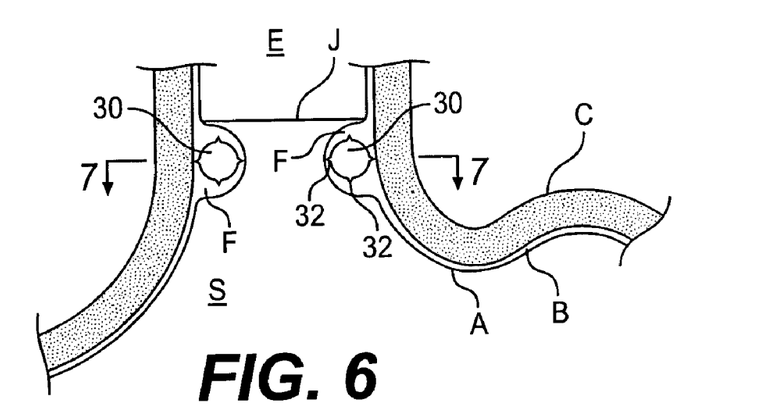
FIG. 6 is a schematic view showing placement of implants in the gastroesophageal junction during a GERD treatment procedure according to the invention.
Figure 7:
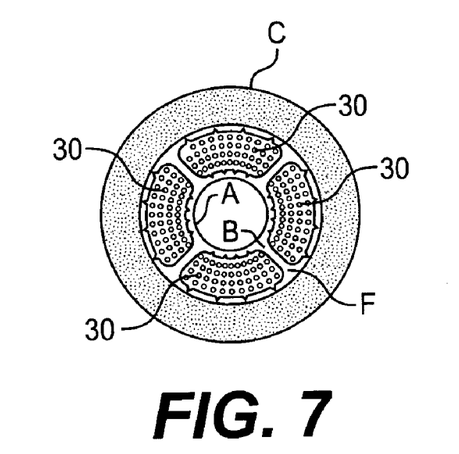
FIG. 7 is a schematic cross sectional view taken along line 7—7 of FIG. 6.
Figure 8:
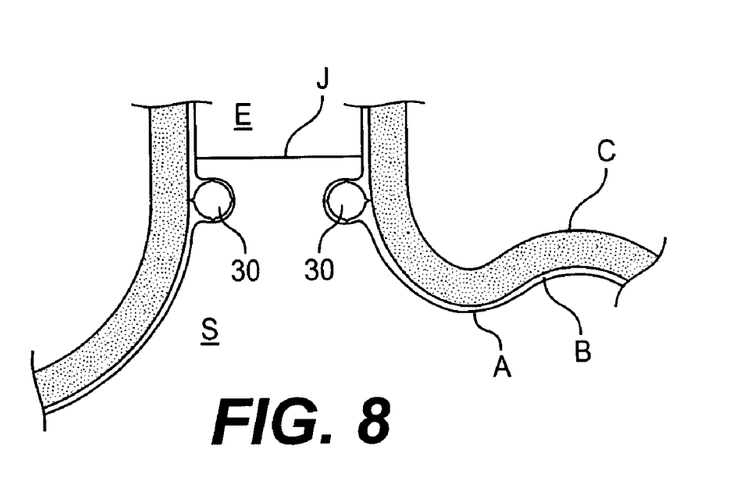
FIG. 8 is a schematic view similar to FIG. 6 showing the implant placement without fluid for separating tissue layers.
Figure 9:
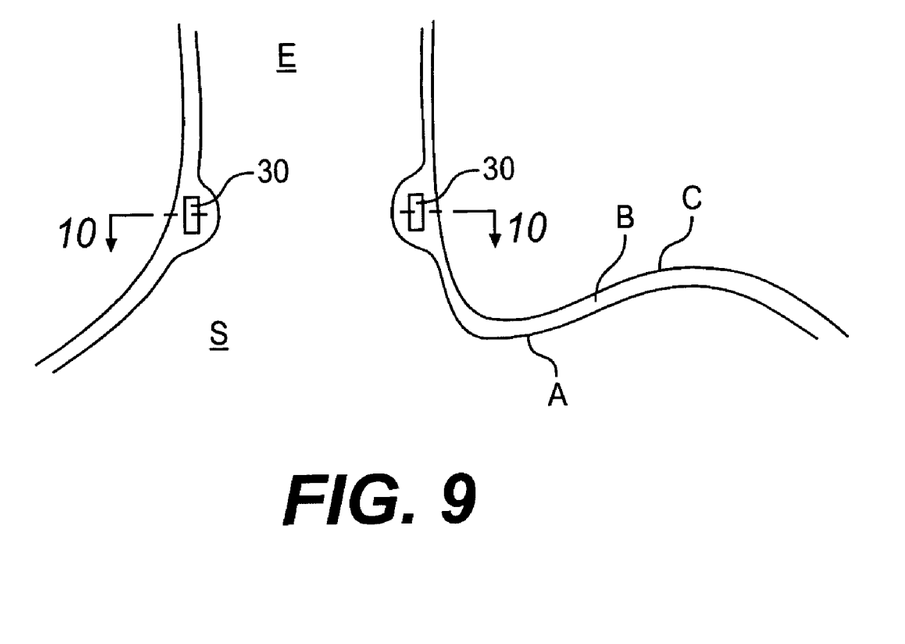
FIG. 9 is a schematic view similar to FIG. 7 showing an alternative GERD treatment procedure wherein implants are substantially parallel to the longitudinal axis of the esophagus.
Figure 10:
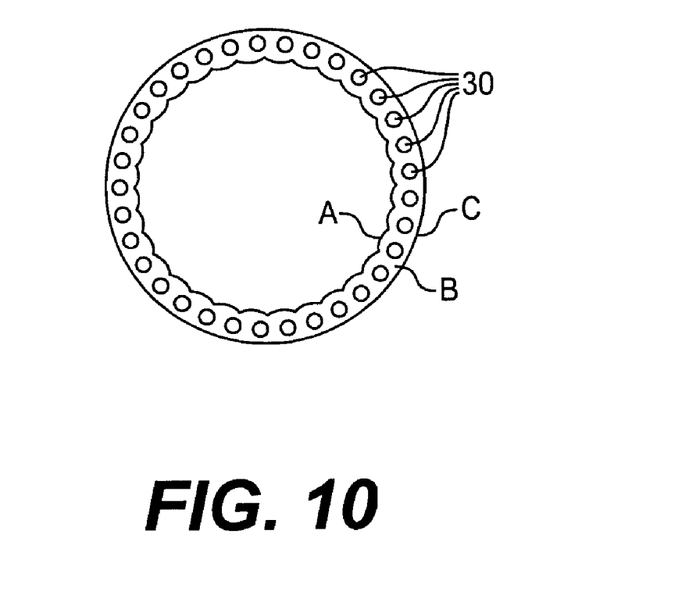
FIG. 10 is a schematic cross sectional view taken along line 10—10 of FIG. 9.

FIGS. 6–8 show an example of how the implants 30 are preferably placed at multiple locations in the submucosa layer B located between the esophagus E and stomach S and slightly below the gastro-esophageal junction J. As shown in FIGS. 6–7, the implants 30 are placed so that the longitudinal axes of the implants 30 are in a plane substantially perpendicular to the longitudinal axis of the esophagus E. However, other configurations are possible. For example, FIGS. 9 and 10 show the implants 30 placed in the tissue layers so that the axes of implants 30 are substantially parallel to the axis of the esophagus E.

When the implants 30 are positioned, as shown in FIGS. 6–8, so that the axes of the implants 30 are in a plane that is substantially perpendicular to the axis of the esophagus E, the elongated member 20, 20' is preferably curved or bent, for example, like the member 20A shown in FIG. 12, to facilitate placing the implants 30 in the tissue while the elongated member 20, 20' extends along the esophagus E. For example, the elongated member 20, 20' could have a bend or curve that positions the axis of the distal end portion of the elongated member 20, 20' in a plane substantially perpendicular to the axis of the remaining portion of the elongated member 20, 20'. FIGS. 6 and 7 show the implants 30 suspended in fluid F used to separate the layers of tissue. Preferably, the structure that was used to introduce this fluid F, such as the second opening 25, second lumen 23, and second fluid source 52, is also used to remove the fluid F to secure the implants 30 in place between the tissue layers. Alternatively, the fluid F is absorbed into the body. FIG. 8 shows the placement of the implants 30 after the fluid is removed or absorbed.

Preferably the implants 30 bulk the tissue at or near the gastro-esophageal junction so that the bulked tissue assists the lower esophageal sphincter to limit reverse flow of stomach contents into the esophagus. Depending on the amount of bulking required, the implants 30 do not always needs to be located directly at the gastro-esophageal junction. Because the implants 30 are preferably compressible and flexible, they allow for relatively normal digestion. If necessary, additional implants 30 could be placed in the tissue at a later time to increase bulking, or the implants 30 could be removed from the tissue in an endoscopic mucosectomy procedure.

Although the implant according to the invention is preferably used to bulk tissue at or near the gastro-esophageal junction in a GERD treatment procedure, the implant could be used to bulk many different types body tissue in different types of procedures. For example, the implant could be used to bulk tissue along the urinary tract in a urinary incontinence treatment.

It will be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the following claims and their equivalents.

What is claimed is:

1. A system for bulking body tissue, comprising:
   an elongated member comprising a proximal end, a distal end, at least one opening in the distal end, and at least one inner lumen extending from the proximal end to the opening in the distal end;
   at least one compressible bulking device in the inner lumen of the elongated member, the at least one bulking device being configured to be implanted in body tissue to bulk the tissue; and
   a pushing device to push the at least one bulking device through the opening in the distal end of the elongated member,
   wherein the at least one bulking device is expandable from a compressed configuration to an expanded configuration, the at least one bulking device being in the compressed configuration when the at least one bulking device is in the inner lumen and the at least one bulking device expanding to the expanded configuration when the at least one bulking device passes through the opening in the distal end of the elongated member,
   wherein the at least one bulking device comprises a migration limiting element for limiting migration of the at least one bulking device in the body tissue, and
   wherein the elongated member comprises a first inner lumen containing the at least one bulking device and a second inner lumen in fluid communication with a source of fluid.

2. The system of claim 1, wherein the second inner lumen is configured to provide fluid to a space between layers of body tissue to separate the layers of body tissue.

3. The system of claim 1, wherein the first inner lumen and the second inner lumen each extend from the proximal end of the elongated member to a respective opening in the distal end of the elongated member.

4. The system of claim 1, wherein the second inner lumen is at least partially disposed within the first inner lumen.

5. The system of claim 1, wherein the second inner lumen has one of a substantially circular cross section and a generally flattened cross section.

6. A system for bulking body tissue, comprising:
   an elongated member comprising a proximal end, a distal end, a curved portion proximate the distal end, at least one opening in the distal end, and at least one inner lumen extending from the proximal end and through the curved portion to the opening in the distal end, the inner lumen being curved near the distal end;
   at least one compressible bulking device in the inner lumen of the elongated member, the at least one bulking device being configured to be implanted in body tissue to bulk the tissue; and
   a pushing device to push the at least one bulking device through the opening in the distal end of the elongated member,
   wherein the elongated member comprises a first inner lumen containing the at least one bulking device and a second inner lumen in fluid communication with a source of fluid.

7. The system of claim 6, wherein the second inner lumen is configured to provide fluid to a space between layers of body tissue to separate the layers of body tissue.

8. The system of claim 6, wherein the first inner lumen and the second inner lumen each extend from the proximal end of the elongated member to a respective opening in the distal end of the elongated member.

9. The system of claim 6, wherein the second inner lumen is at least partially disposed within the first inner lumen.

* * * * *